(12) United States Patent
Yoon et al.

(10) Patent No.: US 9,591,849 B2
(45) Date of Patent: Mar. 14, 2017

(54) MATRIX TYPE ANTIMICROBIAL VEHICLE AND MANUFACTURING METHOD THEREOF

(75) Inventors: Hye Sung Yoon, Daejeon (KR); Hyun Kyoon Kim, Daejeon (KR); Wang Soo Shin, Daejeon (KR); Sun Woo Kim, Daejeon (KR)

(73) Assignee: SAMYANG BIOPHARMACEUTICALS CORPORATION (KR)

(*) Notice: Subject to any disclaimer, the term of this patent is extended or adjusted under 35 U.S.C. 154(b) by 659 days.

(21) Appl. No.: 13/977,067

(22) PCT Filed: Dec. 27, 2011

(86) PCT No.: PCT/KR2011/010153
§ 371 (c)(1),
(2), (4) Date: Jun. 28, 2013

(87) PCT Pub. No.: WO2012/091408
PCT Pub. Date: Jul. 5, 2012

(65) Prior Publication Data
US 2013/0280313 A1    Oct. 24, 2013

(30) Foreign Application Priority Data
Dec. 31, 2010 (KR) .......................... 10-2010-0139910

(51) Int. Cl.
| | | |
|---|---|---|
| *A01N 25/34* | (2006.01) | |
| *A61L 27/50* | (2006.01) | |
| *A61L 27/54* | (2006.01) | |
| *A01N 25/10* | (2006.01) | |
| *A61L 31/14* | (2006.01) | |
| *A61L 31/16* | (2006.01) | |
| *A01N 31/16* | (2006.01) | |
| *A61K 31/085* | (2006.01) | |
| *A61K 9/70* | (2006.01) | |

(52) U.S. Cl.
CPC ............. *A01N 25/10* (2013.01); *A01N 25/34* (2013.01); *A01N 31/16* (2013.01); *A61K 9/7061* (2013.01); *A61K 31/085* (2013.01); *A61L 27/50* (2013.01); *A61L 27/54* (2013.01); *A61L 31/14* (2013.01); *A61L 31/16* (2013.01); *A61L 2300/406* (2013.01); *A61L 2300/604* (2013.01)

(58) Field of Classification Search
CPC ......... A61L 2300/404; A61L 2300/406; A61L 2300/408; A01N 25/34
See application file for complete search history.

(56) References Cited

U.S. PATENT DOCUMENTS

| | | | |
|---|---|---|---|
| 3,629,477 A | 12/1971 | Model et al. | |
| 5,614,310 A * | 3/1997 | Delgado | ............... A61F 13/023 428/316.6 |
| 5,976,565 A | 11/1999 | Fotinos | |
| 7,513,093 B2 | 4/2009 | Scalzo et al. | |
| 2005/0249791 A1* | 11/2005 | Hobbs | .................... A01N 25/34 424/443 |
| 2007/0021835 A1* | 1/2007 | Edidin | .................... A61F 2/441 623/17.12 |
| 2010/0190004 A1 | 7/2010 | Gibbins et al. | |

FOREIGN PATENT DOCUMENTS

| | | |
|---|---|---|
| JP | 2005-120008 A | 5/2005 |
| KR | 10-2007-0014190 A | 1/2007 |
| WO | WO 2010/080936 A2 | 7/2010 |

OTHER PUBLICATIONS

International Search Report from International Application No. PCT/KR2011/010153 mailed Aug. 30, 2012.
Extended European Search Report for European Patent Application No. 11 854 166.3 (mailed Jul. 22, 2014).
Solutia Inc., "Gelva Multipolymer Solution 737 MSDS", Solutia Inc., Material Safety Data Sheets, 1-9 (Dec. 19, 2001).

* cited by examiner

*Primary Examiner* — Michael B Pallay
(74) *Attorney, Agent, or Firm* — Merchant & Gould P.C.

(57) ABSTRACT

Provided is a matrix type antimicrobial vehicle, including: a matrix layer comprising an antimicrobial agent and an adhesive; an antimicrobial agent-releasing layer formed on one surface of the matrix layer; and a release liner formed on the other surface of the matrix layer, and a method for preparing the same. The matrix type antimicrobial vehicle is incorporated into a package having a medical kit so that the antimicrobial agent is released to the surface of medical kit or package continuously. Therefore, it is possible for the surface of the medical kit or package to maintain a constant concentration of antimicrobial agent continuously even when the medical kit or package is stored for a long time.

22 Claims, 1 Drawing Sheet

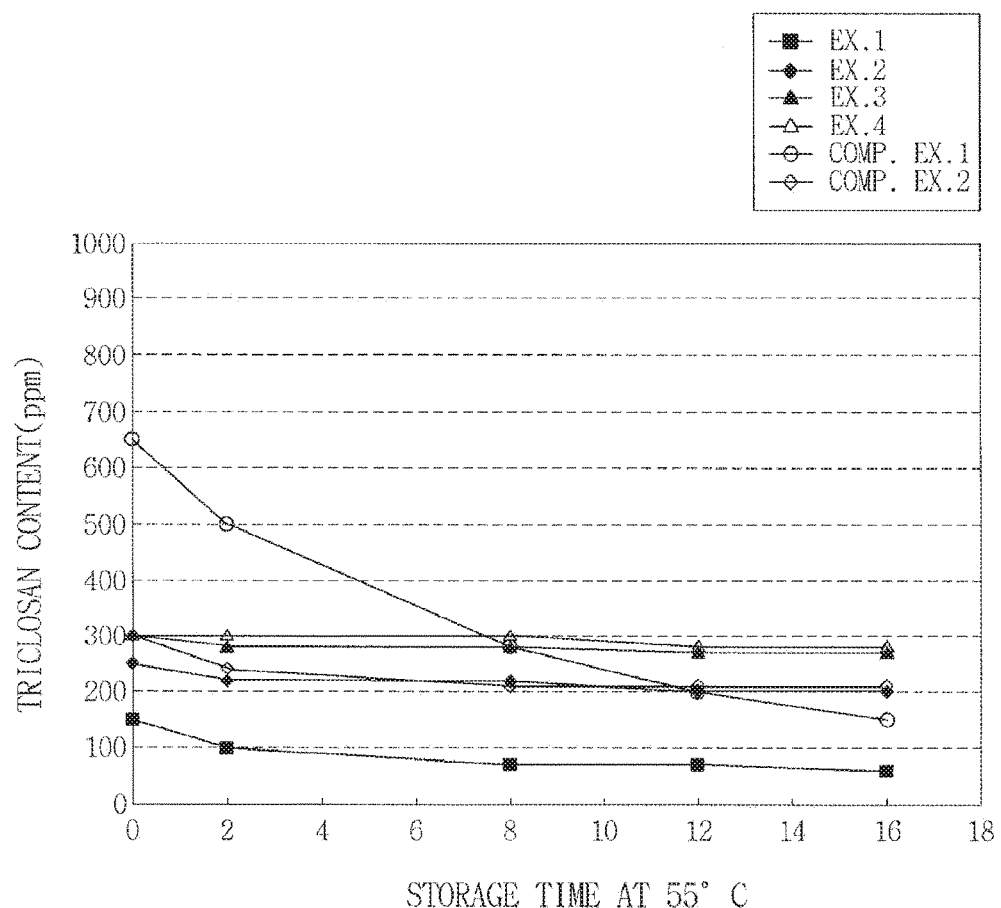

MATRIX TYPE ANTIMICROBIAL VEHICLE AND MANUFACTURING METHOD THEREOF

This application is a U.S. National Stage Application under 35 U.S. C. §371 of International Patent Application No. PCT/KR2011/010153, filed 27 Dec. 2011, which claims the benefit of priority to Korean Patent Application No. 10-2010-0139910, filed 31 Dec. 2010, the disclosures of all of which are hereby incorporated by reference in their entireties. The International Application was published in English on 5 Jul. 2012 as WO 2012/091408.

TECHNICAL FIELD

This disclosure relates to an antimicrobial source from which an antimicrobial agent is released continuously onto the surface of a medical device, and more particularly, to a matrix type antimicrobial vehicle capable of minimizing a decrease in antimicrobial agent content on the surface of a medical device during the storage thereof.

BACKGROUND ART

When medical devices or medical instruments are allowed to be in contact with patients, they are always exposed to the risk of infection. Particularly, medical kits inserted into the human body are in direct contact with tissues in vivo or body fluid, thereby increasing the risk of infection. To reduce the risk of infection, there has been an attempt to introduce an anti-infectious agent to medical kits.

Typically, there have been commercially available products formulated into mouth cleaners or toothpastes using the antimicrobial effect of triclosan. In addition, U.S. Pat. No. 7,513,093 discloses antimicrobial suture thread obtained by coating suture thread for surgery with triclosan. More particularly, a triclosan antimicrobial agent is mixed with a solvent, and then the surface of suture thread is coated with the resultant mixture to provide the surface with a triclosan antimicrobial agent.

However, it is required to introduce an antimicrobial agent to medical kits in an amount sufficient to maintain the anti-infectious effect for a sufficient period of time during which the medical kits are used. Such an amount of antimicrobial agent may adversely affect the surface properties of the medical kits or may exhibit cytotoxicity in addition to the antimicrobial effect. In addition, it is required for the medical kits including an anti-infectious agent to maintain anti-infectious activity to a desired level during their use in vivo.

Therefore, there has been a need for developing technology of maintaining antimicrobial activity for a long period of time by introducing an adequate amount of antimicrobial agent to medical kits while not adversely affecting the surface properties of the medical kits or exhibiting cytotoxicity.

DISCLOSURE OF INVENTION

Technical Problem

This disclosure is directed to providing a matrix type antimicrobial vehicle that allows an antimicrobial agent to be released continuously to the surface of a medical device, thereby minimizing a decrease in antimicrobial agent content on the surface of the medical device during the storage thereof.

Solution to Problem

In one general aspect, there is provided a matrix type antimicrobial vehicle, comprising: a matrix layer comprising an antimicrobial agent and an adhesive; an antimicrobial agent-releasing layer formed on one surface of the matrix layer; and a release liner formed on the other surface of the matrix layer.

In another general aspect, there is provided a method for preparing a matrix type antimicrobial vehicle, comprising: applying an adhesive solution containing an antimicrobial agent and an adhesive onto an antimicrobial agent-releasing layer or a release liner; drying the adhesive solution to form a matrix layer; and stacking a release liner on one surface of the matrix layer if the other surface of the matrix layer is attached to the antimicrobial agent-releasing layer, or stacking an antimicrobial agent-releasing layer on one surface of the matrix layer if the other surface of the matrix layer is attached to the release liner.

In still another general aspect, there is provided a method for manufacturing an antimicrobial medical kit, comprising: exposing an implantable medical kit to the above-mentioned matrix type antimicrobial vehicle; and subjecting the medical kit and the matrix type antimicrobial vehicle to temperature, time and pressure conditions sufficient to allow an effective amount of antimicrobial agent to be released from the matrix type vehicle toward the medical kit.

In yet another general aspect, there is provided a method for manufacturing an antimicrobial medical kit, comprising: disposing an implantable medical kit and the above-mentioned matrix type antimicrobial vehicle in a package; and subjecting the package, the medical kit and the matrix type antimicrobial vehicle to temperature, time and pressure conditions sufficient to allow an effective amount of antimicrobial agent to be released from the matrix type vehicle toward the medical kit or the package.

Advantageous Effects of Invention

The antimicrobial vehicle disclosed herein is included in a package having a medical kit so that an antimicrobial agent may be released continuously to the surface of the medical kit or package. As a result, it is possible to maintain a desired level of antimicrobial agent content on the surface of the medical kit or package even when the medical kit or package is stored for a long time.

BRIEF DESCRIPTION OF DRAWINGS

The above and other aspects, features and advantages of the disclosed exemplary embodiments will be more apparent from the following detailed description taken in conjunction with the accompanying drawings in which:

The FIGURE is a graph illustrating the triclosan content detected in medical suture thread with time during the storage thereof at 55° C., when the matrix type vehicles according to Examples 1-4 and Comparative Example 1 are applied to the medical suture thread.

BEST MODE FOR CARRYING OUT THE INVENTION

Hereinafter, the embodiments of the present disclosure will be described in detail.

As used herein, the term 'antimicrobial vehicle' means a vehicle used for the purpose of applying an antimicrobial agent to a medical device or package in a package including a medical kit. In addition, the term 'medical kit' includes any medical kit, medical device, therapeutic or supplementary instruments for use in surgery, or the like.

According to one embodiment, the matrix type antimicrobial vehicle comprises an antimicrobial agent-releasing layer, a matrix layer and a release liner, stacked successively.

According to one embodiment, the antimicrobial agent may include, but is not limited to, halogenated hydroxyl ether, acyl oxydiphenyl ether or a combination thereof. For example, the antimicrobial agent may include those disclosed in U.S. Pat. No. 3,629,477, and particular examples thereof include halogenated 2-hydroxydiphenyl ether and/or halogenated 2-acyloxy diphenyl ether. More particularly, 2,4,4'-trichloro-2'-hydroxydiphenyl ether, also called triclosan, may be used as the antimicrobial agent. Triclosan has an antimicrobial effect against various microorganisms related to infection after surgery or infection at the site of surgery. Non-limiting examples of such microorganisms include *Staphylococcus, Staphylococcus epidermidis, Staphylococcus aureus*, methicillin-resistant *Staphylococcus epidermidis*, methicillin-resistant *Staphylococcus aureus* and a combination thereof.

According to one embodiment, the antimicrobial agent may be used in the matrix layer composition in an amount of 0.1-80 wt %, particularly 10-60 wt % based on the total weight of the composition. When the antimicrobial agent is used in an amount less than 0.1 wt %, an undesirably low amount of antimicrobial agent is applied to a medical kit, and thus the resultant medical kit may not provide sufficient antimicrobial activity. On the other hand, the antimicrobial agent is used in an amount greater than 80 wt %, the antimicrobial agent could not be dissolved enough and be precipitated. Also, when an undesirably high amount of triclosan is applied to a medical kit, the resultant medical kit may cause toxicity due to such an excessive amount of triclosan.

According to one embodiment, the adhesive may include a non-aqueous acrylic polymer. Such non-aqueous acrylic polymers have higher adhesion and adhesion durability as compared to aqueous polymers that have been used as an adhesive in general plasters, or the like. In addition, the antimicrobial agent used herein is practically insoluble in water and has a low melting point (55-57° C.), and thus shows high solubility to an organic solvent in which a non-aqueous acrylic polymer is dissolved. Therefore, it is possible to increase the concentration of antimicrobial agent in the matrix layer when using such non-aqueous acrylic polymers. In addition, it is possible to realize controlled release by controlling the antimicrobial agent release at the initial time. As a result, the antimicrobial vehicle disclosed herein shows excellent antimicrobial activity for at least one year, particularly for at least 3 years, while not exhibiting a decrease in the content of antimicrobial agent on the surface of a medical kit or package. Further, it is possible to reduce the amount of adhesive used in the matrix layer and to reduce the thickness of vehicle, for example, to 30-300 μm, particularly to 100-200 μm by using such non-aqueous acrylic polymers having high adhesion durability. Therefore, there is no need for changing the design of a medical kit package.

According to one embodiment, the non-aqueous acrylic polymer may include, but is not limited to, a homopolymer of any one monomer selected from 2-ethylhexyl acrylate, vinyl acrylate and vinylacrylic acid, or a copolymer of two or more monomers selected therefrom.

According to one embodiment, the adhesive may be used in the matrix layer composition in an amount of 20-99.9 wt %, particularly 40-85 wt % based on the total weight of the composition. When the adhesive is used in an amount less than 20 wt %, the matrix layer and the matrix type vehicle using the matrix layer may not have sufficient adhesive property. On the other hand, when the adhesive is used in an amount greater than 99.9 wt %, it is difficult to support the antimicrobial agent enough in the matrix layer.

According to one embodiment, the matrix layer may further include a surfactant. Particular examples of the surfactant may include anionic, cationic, amphoteric and non-ionic surfactants, and more particularly non-ionic surfactants. The non-ionic surfactants control the delivery of an antimicrobial agent, and thus control the initial release amount of an antimicrobial agent.

According to one embodiment, the surfactant may be used in the matrix layer composition in an amount of 0.1-30 wt %, particularly 1-15 wt % based on the total weight of the composition. Surfactants control the release of an antimicrobial agent to a certain upper limit of amount, but provide no improvement in release control beyond the limit.

Particular examples of the non-ionic surfactant include at least one selected from the group consisting of glycerol monolaurate, glycerol monooleate, glycerol monolinolate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate, oleyl oleate, sorbitan monolaurate, sorbitan monooleate, polyoxyethylene lauryl ether, polyoxyethylene cetyl ether, polyoxyethylene stearyl ether, polyoxyethylene oleyl ether, polyoxyethylene stearate, polyoxyethylene-9-nonyl phenyl ether, polyethylene glycol-40 hydrogenated castor oil, polyethylene glycol-35 castor oil, octocinol-11, fatty acid esters of Tween, and fatty acid esters of Span. More particularly, a surfactant selected from the group consisting of sorbitan monooleate, glycerol monolaurate, glycerol monooleate and sorbitan monolaurate, or a combination thereof may be used.

According to one embodiment, the matrix layer may further include alcohol. Particularly, the alcohol may be one having a molecular weight of 600 daltons or less. The antimicrobial agent used herein has high solubility to alcohol having a low molecular weight of 600 daltons or less. Therefore, it is possible to further accelerate the release of the antimicrobial agent dissolved in the matrix layer containing such alcohol with high solubility under the conditions of a predetermined temperature, time and pressure.

According to one embodiment, the alcohol having a molecular weight of 600 daltons or less may be a C1-C12 alcohol. Particular examples of such alcohols include at least one selected from the group consisting of methanol, ethanol, isopropanol, butanol, benzyl alcohol, triacetin, transcutol, propylene glycol, glycerin and polyethylene glycol having a molecular weight of 600 daltons or less. More particularly, ethanol or isopropanol may be used.

According to one embodiment, the alcohol may be used in the matrix layer composition in an amount of 1-30 wt %, particularly 1-5 wt % based on the total weight of the composition. Such alcohols improve the solubility of an antimicrobial agent and delivery of an antimicrobial agent toward the exterior to a certain upper limit of amount, but decrease the adhesive concentration beyond the limit.

According to one embodiment, when the matrix layer further includes a surfactant and alcohol, the surfactant and alcohol may be present in the matrix layer in a weight ratio between 1:1 and 1:4. Such a weight ratio allows the initial release control of an antimicrobial agent.

According to one embodiment, the antimicrobial agent-releasing layer may be in the form of a porous film or non-woven web, and may include at least one material selected from the group consisting of polyester, polyurethane, polyethylene and rayon. The antimicrobial agent-releasing layer covers the matrix layer containing an antimicrobial agent, and assists the antimicrobial agent in diffusing from the matrix layer so that it may be applied to the surface of a medical kit or package.

According to one embodiment, the release liner covers and protects the matrix layer containing an antimicrobial agent before the matrix type vehicle is attached to a medical device package, etc., and then is removed right before it is attached thereto. Such release liners may include currently used antimicrobial agent-impermeable films.

In another general aspect, there is provided a method for preparing a matrix type antimicrobial vehicle, including: applying an adhesive solution containing an antimicrobial agent and an adhesive onto an antimicrobial agent-releasing layer or a release liner; drying the adhesive solution to form a matrix layer; and stacking a release liner on one surface of the matrix layer if the other surface of the matrix layer is attached to the antimicrobial agent-releasing layer, or stacking an antimicrobial agent-releasing layer on one surface of the matrix layer if the other surface of the matrix layer is attached to the release liner.

According to one embodiment, the antimicrobial agent in the matrix layer may include halogenated hydroxyl ether, acryloxydiphenyl ether or a combination thereof, and the adhesive may include a non-aqueous acrylic polymer.

According to one embodiment, the matrix layer may further include at least one of a non-ionic surfactant and alcohol having a molecular weight of 600 daltons or less.

Particular types and weights of the materials forming the matrix layer are the same as described above. In addition, particular types and weights of the materials forming the antimicrobial agent-releasing layer are the same as described above.

According to one embodiment, the method may further include applying an adhesive solution containing a non-ionic surfactant, alcohol having a molecular weight of 600 daltons or less or a combination thereof to at least one layer of the antimicrobial agent-releasing layer and the release liner to form an adhesive layer.

When preparing the adhesive solution, the above-mentioned adhesive may be dissolved in an organic solvent such as n-hexane, toluene or ethyl acetate to provide the adhesive solution. Then, an antimicrobial agent may be dissolved in the adhesive solution. In addition, at least one of the above-mentioned surfactant and alcohol having a molecular weight of 600 daltons or less may be further incorporated to the adhesive solution.

When applying the adhesive solution, the solution containing the above-mentioned volatile ingredients may be sprayed or applied in a predetermined amount through a nozzle.

After the application, the adhesive solution may be dried at a high temperature of 80-120° C. for a short time of 1-10 minutes so that the organic solvent contained in the adhesive solution may be evaporated and removed.

In still another general aspect, there is provided an antimicrobial medical kit package including an implantable medical kit and the matrix type antimicrobial vehicle disclosed herein.

The antimicrobial vehicle disclosed herein may be applied to, but is not limited to, implantable medical kits, for example, suture thread for surgery such as multifilament or monofilament thread, mesh, clips, anchors for surgery, absorptive pins and screws for orthopedics, anti-adhesive mesh and anti-adhesive films, hernia supporting devices, stents, catheters, and packages including them. Any absorptive and non-absorptive implantable medical kits may be included in the scope of this disclosure. The medical devices or packages to which the antimicrobial vehicle disclosed herein is applied may include a preliminarily provided antimicrobial agent or not.

The matrix type antimicrobial vehicle obtained by the method is attached to a medical kit or package, and serves as a source from which an antimicrobial agent is supplied to the medical kit or package.

In still another general aspect, there is provided a method for manufacturing an antimicrobial medical kit, including: exposing an implantable medical kit to the above-mentioned matrix type antimicrobial vehicle; and subjecting the medical kit and the matrix type antimicrobial vehicle to temperature, time and pressure conditions sufficient to allow an effective amount of antimicrobial agent to be released from the matrix type vehicle toward the medical kit. The temperature, time and pressure conditions sufficient for carrying out the method may include 30-80° C., 3-19 hours, and ambient pressure or reduced pressure.

In yet another general aspect, there is provided a method for manufacturing an antimicrobial medical kit, including: disposing an implantable medical kit and the above-mentioned matrix type antimicrobial vehicle in a package; and subjecting the package, the medical kit and the matrix type antimicrobial vehicle to temperature, time and pressure conditions sufficient to allow an effective amount of antimicrobial agent to be released from the matrix type vehicle toward the medical kit or the package. The temperature, time and pressure conditions sufficient for carrying out the method may include 30-80° C., 3-19 hours, and ambient pressure or reduced pressure.

In general, a medical kit is sterilized or dried in a package. When the matrix type antimicrobial vehicle is attached to a medical device package, it allows release of the antimicrobial agent so that the antimicrobial agent is applied to a medical device or package. In addition, during the storage of the package, the matrix type antimicrobial vehicle allows continuous release of the antimicrobial agent so that the surface of the medical device maintains a constant concentration of antimicrobial agent. The package or medical kit is sterilized or dried after the matrix type antimicrobial vehicle is disposed in the package having the medical kit. The sterilization or drying may be carried out under the conditions sufficient for an effective amount of antimicrobial agent to be released from the vehicle toward the medical kit or package. For example, such conditions include 30-80° C., 3-19 hours, and ambient pressure or reduced pressure. In this manner, the antimicrobial agent is applied to the surface of the medical kit or package.

The examples and experiments will now be described. The following examples and experiments are for illustrative purposes only and not intended to limit the scope of this disclosure.

Test Example 1

Preparation of Matrix Type Antimicrobial Vehicle and Determination of Inhibition Zone Against Growth of Microorganisms A matrix layer containing an antimicrobial agent was disposed between an antimicrobial agent-releasing layer and a release liner, followed by lamination, to provide matrix type vehicles (Examples 1-4), in the same manner as described hereinafter. Each matrix layer had the composition as shown in the following Table 2.

First, an acrylate adhesive (National Starch & Duro-Tak, 87-2196) was introduced to a 50 mL sample container. Next, triclosan (antimicrobial agent) was added in the amount as shown in Table 2 thereto, and the resultant adhesive solution was agitated under 200 rpm until a completely homogeneous solution was obtained. To remove air bubbles from the adhesive solution, the adhesive solution was left as it was for at least 10 minutes.

Then, the adhesive solution was applied to a release film (3; 3M Scotchpak 9744, 1022, 3M paper release liner 1361, 9743) and dried with a Lab coater and Dryer (Mathis, Switzerland) at a high temperature of 80-120° C. for 8-12 minutes to form a release film and a matrix layer.

A nonwoven web as an antimicrobial agent-releasing layer (Vilene nonwoven polyester, 3M nonwoven polyurethane 9905, 3M spunlaced nonwoven polyester 1538, 3M rayon nonwoven 1533, 3M rayon acetate) was disposed on the preliminarily formed matrix layer, followed by lamination, to provide a matrix type vehicle with a size of 2 cm×2 cm.

The matrix type vehicle was attached to medical paper and Neosorb suture thread (Samyang Co.) was wound to an adequate size. Next, the suture thread was wrapped with the paper and introduced into an aluminum package, followed by drying at 20-60° C. for about 5 hours under nitrogen atmosphere alternating with reduced pressure. Then, the package was sterilized at 40-80° C. for about 2-8 hours while humidifying it to a humidity of 10-60% and introducing ethylene oxide gas thereto. The package was dried at 40-80° C. under reduced pressure for about 4-16 hours in order to remove the residual ethylene oxide gas and to dry off moisture.

Then, the suture thread was removed from the package, and the content of the antimicrobial agent present on the surface of the suture thread was determined by HPLC according to the operating conditions as shown in the following Table 1. The results are shown in Table 2. To determine the content of the antimicrobial agent, the suture thread was cut into a length of 1 cm or less and sampled precisely in an amount of 500 mg. The suture thread sample was introduced to 10 mL of methanol and agitated under 150 rpm for 1 hour. The methanol solution was filtered through a 0.45 μm syringe filter, and 2 mL of the filtrate was taken as a test sample for determining the triclosan content.

In Comparative Example 1, Kraft paper was dipped in 5 wt % triclosan solution and dried. Then, the sample was subjected to sterilization under the same condition as Examples 1-4 and the content of the antimicrobial agent was determined. In Comparative Example 2, the matrix layer was formed to have the same composition as Example 2, except that the vehicle had no antibacterial agent-releasing layer. The content of the antimicrobial agent was determined in the same manner as mentioned above.

TABLE 1

| | | |
|---|---|---|
| 1) | Instrument | High-speed liquid chromatography |
| 2) | Column | Column with an inner diameter of 4.6 mm and length of 150 mm, packed with octadecyl-silylated silica gel, or a similar column |
| 3) | Mobile phase | 6.5 g of sodium hydrogen phosphate is dissolved into 1000 mL of water, 1000 mL of isopropyl alcohol is added thereto, followed by mixing, and 6 g of sodium lauryl sulfate is added and dissolved to provide a solution. Then, the solution is adjusted to pH 3.0 by adding phosphoric acid thereto to provide a mobile phase. |
| 4) | Flow rate | 1.0 mL/min. |
| 5) | Temperature | 40° C. |
| 6) | Loading amount | 10 μL |
| 7) | Detector | UV absorption spectrometer (239 nm) |

TABLE 2

| | Composition of matrix layer (wt %) | | | | Content of antimicrobial agent on surface of suture thread (μg/g) |
|---|---|---|---|---|---|
| | TriclosanUSP | Acrylate adhesive | Ethanol | Sorbitan mono-oleate | |
| Ex. 1 | 20 | 80 | — | — | 150 |
| Ex. 2 | 25 | 75 | — | — | 250 |
| Ex. 3 | 28 | 70 | 6 | 6 | 300 |
| Ex. 4 | 28 | 70 | 3 | 9 | 300 |
| Comp. Ex. 1 | | | | | 650 |
| Comp. Ex. 2 | 25 | 75 | — | — | 300 |

In addition, the suture thread was removed from the packages of Examples 1-4 and Comparative Examples 1-2. Based on KISO20645, a test zone of inhibition against growth of microorganisms was determined by a disk diffusion method. The results are shown in the following Table 3. More particularly, Staphylococcus strains grown in trypsin-digested soybean broth at 37° C. for 24 hours were diluted with sterilized 0.85% saline to a concentration of $1 \times 10^6$-$10^8$ cfu (colony forming units)/mL. For the lower layer free from bacteria, 10 mL of agar was provided and put into a sterilized Petri dish so that it was consolidated. For the upper layer, 150 mL of agar was inoculated with 1 mL of inoculum having a bacteria concentration of $1.5 \times 10^8$ cfu/mL and stirred thoroughly. Then, 5 mL of agar was poured to each Petri dish and consolidated. Suture thread with a length of 5 cm was allowed to be in contact with the medium and bacteria were cultured at 37° C. for 24 hours. After the culturing, bacteria growth was determined and the inhibition zone was measured. In other words, the distance from the suture thread and the edge of the zone, in which the bacteria growth was inhibited, was measured.

TABLE 3

| Microorganism | NO. | Sample No. | Minimum | Maximum | Average |
|---|---|---|---|---|---|
| Staphylococcus aureus | Ex. 1 | 3 | 10 | 12 | 11 |
| | Ex. 2 | 3 | 14 | 16 | 15 |
| | Ex. 3 | 3 | 22 | 26 | 24 |
| | Ex. 4 | 3 | 20 | 25 | 23 |
| | Comp. Ex. 1 | 3 | 30 | 40 | 35 |
| | Comp. Ex. 2 | 3 | 18 | 24 | 21 |
| Staphylococcus epidermidis | Ex. 1 | 3 | 11 | 12 | 12 |
| | Ex. 2 | 3 | 16 | 18 | 17 |
| | Ex. 3 | 3 | 25 | 27 | 26 |
| | Ex. 4 | 3 | 24 | 26 | 25 |
| | Comp. Ex. 1 | 3 | 35 | 37 | 36 |
| | Comp. Ex. 2 | 3 | 20 | 25 | 23 |

Test Example 2

Evaluation of Content of Antimicrobial Agent Detected in Suture Thread

While each suture thread sample was stored at 55° C., the triclosan content detected from each suture thread sample was evaluated. The results are shown in the FIGURE.

Comparative Example 1 showed a rapid drop in triclosan amount with time. On the contrary, it was shown that the vehicle disclosed herein supplied the antimicrobial agent continuously to the suture thread so that the thread surface maintained a constant triclosan content to provide stable suture thread. As compared to the vehicle disclosed herein, Comparative Example 2 maintained the antimicrobial agent content for a certain period of time but showed a significant drop in antimicrobial agent content at the initial time. It can be seen from the results that the antimicrobial agent-releasing layer serves to prevent excessive release of the antimicrobial agent at the initial time and to maintain the antimicrobial agent content constantly.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

We claim:

1. An antimicrobial medical kit package, comprising an implantable medical kit and a matrix type antimicrobial vehicle, wherein the matrix type antimicrobial vehicle comprises:
  a matrix layer comprising an antimicrobial agent and an adhesive;
  an antimicrobial agent-releasing layer formed on one surface of the matrix layer; and
  a release liner formed on the other surface of the matrix layer;
  wherein an effective amount of antimicrobial agent can be released from the matrix type antimicrobial vehicle toward the medical kit when the medical kit and the matrix type antimicrobial vehicle are subjected to a temperature, time and pressure sufficient to allow an effective amount of antimicrobial agent to be released from the matrix type vehicle toward the medical kit.

2. The antimicrobial medical kit package according to claim 1, wherein the antimicrobial agent comprises a halogenated hydroxyl ether, acyl oxydiphenyl ether or a combination thereof.

3. The antimicrobial medical kit package according to claim 2, wherein the antimicrobial agent is used in the matrix layer in an amount of 0.1-80 wt % based on the total weight of a composition forming the matrix layer.

4. The antimicrobial medical kit package according to claim 1, wherein the adhesive comprises a non-aqueous acrylic polymer.

5. The antimicrobial medical kit package according to claim 4, wherein the non-aqueous acrylic polymer is a homopolymer of any one monomer selected from the group consisting of 2-ethylhexyl acrylate, vinyl acrylate and vinylacrylic acid, or a copolymer of two or more monomers selected therefrom.

6. The antimicrobial medical kit package according to claim 4, wherein the adhesive is used in the matrix layer in an amount of 20-99.9 wt % based on the total weight of a composition forming the matrix layer.

7. The antimicrobial medical kit package according to claim 1, wherein the matrix layer further comprises at least one selected from surfactants and alcohols.

8. The antimicrobial medical kit package according to claim 7, wherein the surfactant and alcohol are used in a weight ratio between 1:1 and 1:4.

9. The antimicrobial medical kit package according to claim 7, wherein the surfactant is a non-ionic surfactant and is used in the matrix layer in an amount of 0.1-30 wt % based on the total weight of a composition forming the matrix layer.

10. The antimicrobial medical kit package according to claim 7, wherein the alcohol is one having a molecular weight of 600 daltons or less, and is used in the matrix layer in an amount of 0.1-30 wt % based on the total weight of a composition forming the matrix layer.

11. The antimicrobial medical kit package according to claim 7, wherein the surfactant is at least one selected from the group consisting of glycerol monolaurate, glycerol monooleate, glycerol monolinolate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate, oleyl oleate, sorbitan monolaurate, sorbitan monooleate, polyoxyethylene lauryl ether, polyoxyethylene cetyl ether, polyoxyethylene stearyl ether, polyoxyethylene oleyl ether, polyoxyethylene stearate, polyoxyethylene-9-nonyl phenyl ether, polyethylene glycol-40 hydrogenated castor oil, polyethylene glycol-35 castor oil, octocinol-11, polyethoxylated sorbitan esters, and sorbitan esters.

12. The antimicrobial medical kit package according to claim 7, wherein the alcohol is at least one selected from the group consisting of ethanol, isopropanol, butanol, benzyl alcohol, triacetin, transcutol, propylene glycol, glycerin and polyethylene glycol having a molecular weight of 600 daltons or less.

13. The antimicrobial medical kit package according to claim 1, wherein the antimicrobial agent-releasing layer comprises a porous film or non-woven web comprising at least one material selected from the group consisting of polyester, polyurethane, polyethylene and rayon.

14. A method for manufacturing an antimicrobial medical kit package according to claim 1, comprising a method for preparing the matrix type antimicrobial vehicle, comprising:
  applying an adhesive solution comprising an antimicrobial agent and an adhesive onto an antimicrobial agent-releasing layer or a release liner;
  drying the adhesive solution to form a matrix layer; and
  stacking a release liner on one surface of the matrix layer if the other surface of the matrix layer is attached to the antimicrobial agent-releasing layer, or stacking an antimicrobial agent-releasing layer on one surface of the matrix layer if the other surface of the matrix layer is attached to the release liner.

15. The method for manufacturing an antimicrobial medical kit package according to claim 14, wherein the antimicrobial agent in the matrix layer comprises a halogenated hydroxyl ether, acyl oxydiphenyl ether or a combination thereof, and the adhesive comprises a non-aqueous acrylic polymer.

16. The method for manufacturing an antimicrobial medical kit package according to claim 14, wherein the matrix layer further comprises at least one selected from a nonionic surfactant and alcohol having a molecular weight of 600 daltons or less.

17. The antimicrobial medical kit package according to claim 1, wherein the implantable medical kit is selected from the group consisting of suture thread for surgery, mesh for surgery, suture thread clips, suture thread anchors, absorptive pins and screws for orthopedics, anti-adhesive mesh, anti-adhesive films, hernia supporting devices, stents, and catheters.

18. A method for manufacturing an antimicrobial medical kit package according to claim 14, comprising:
exposing an implantable medical kit to the matrix type antimicrobial vehicle; and
subjecting the medical kit and the matrix type antimicrobial vehicle to temperature, time and pressure conditions sufficient to allow an effective amount of antimicrobial agent to be released from the matrix type vehicle toward the medical kit.

19. A method for manufacturing an antimicrobial medical kit package according to claim 14, comprising:
disposing an implantable medical kit and the matrix type antimicrobial vehicle in a package; and
subjecting the package, the medical kit and the matrix type antimicrobial vehicle to temperature, time and pressure conditions sufficient to allow an effective amount of antimicrobial agent to be released from the matrix type vehicle toward the medical kit or the package.

20. The method for manufacturing an antimicrobial medical kit package according to claim 14, wherein the temperature, time and pressure conditions include 30-80° C., 3-19 hours and ambient pressure or reduced pressure.

21. The method for manufacturing an antimicrobial medical kit package according to claim 19, wherein the temperature, time and pressure conditions include 30-80° C., 3-19 hours and ambient pressure or reduced pressure.

22. The antimicrobial medical kit package according to claim 1, wherein the temperature is 30-80° C., the time is 3-19 hours, and the pressure is ambient pressure or reduced pressure.

* * * * *